May 24, 1955 M. TANTAU Plant Pat. 1,395
ROSE PLANT
Filed Sept. 10, 1954
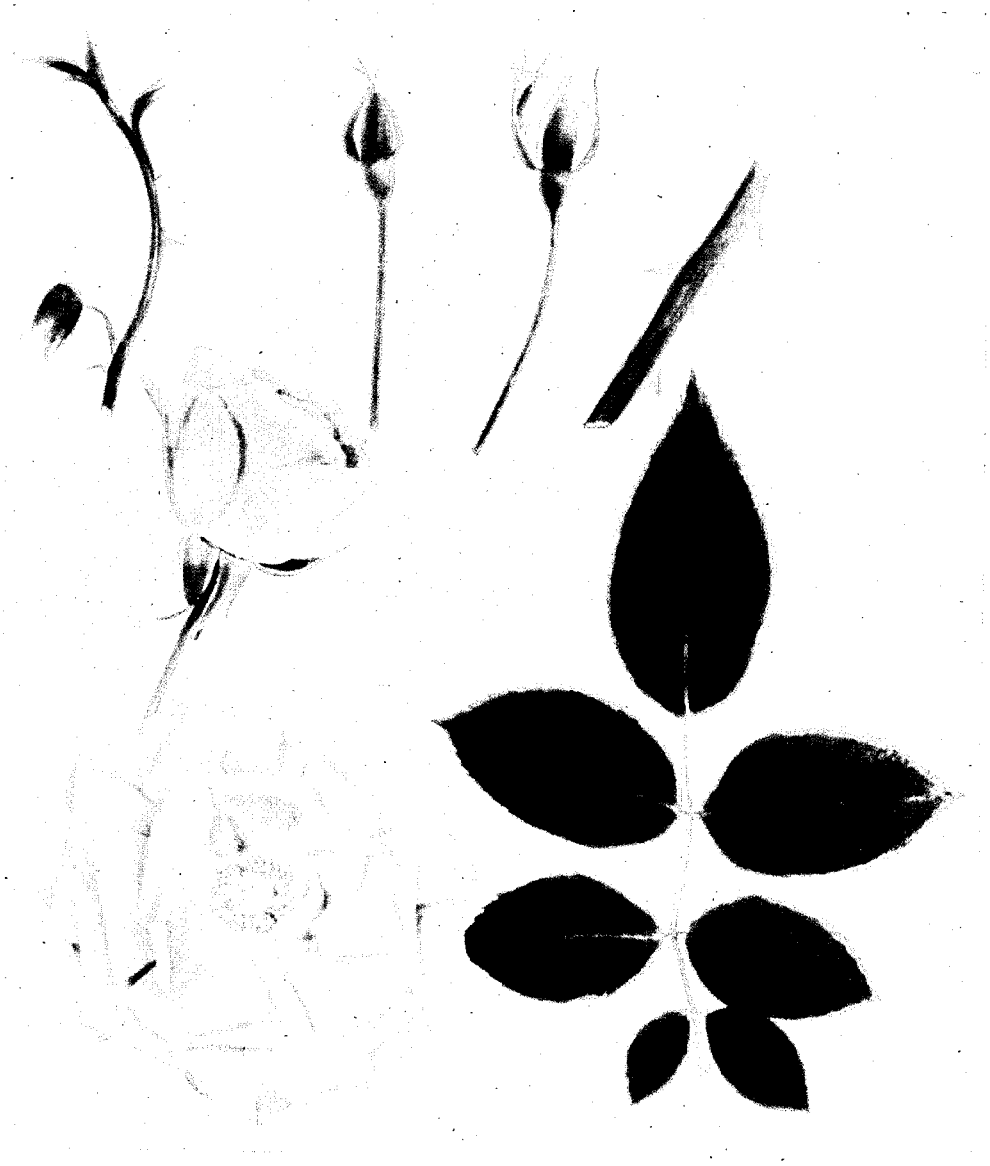
Inventor.
Mathias Tantau
By: Robb & Robb
Attorneys.

United States Patent Office

Plant Pat. 1,395

Patented May 24, 1955

1,395

ROSE PLANT

Mathias Tantau, Uetersen, Holstein, Germany, assignor to Jackson & Perkins Company, Newark, N. Y., a corporation of New York Application September 10, 1954, Serial No. 455,372

1 Claim. (Cl. 47—61)

The present invention relates to a new and distinct variety of rose plant of the large-flowered polyantha class, which was originated by me by crossing the variety "Cinnabar" (unpatented) with an unnamed and unpatented seedling of "Cinnabar" × "Kathe Duvigneau" (unpatented).

The primary objective in making this cross was to produce a new variety of rose which combines the brilliant coloring of the flowers of the variety "Cinnabar" with a better and taller-growing plant habit, the latter characteristic being one of the features of the more vigorous seedling parent which normally produces rather poor flowers. This objective was fully achieved, as evidenced by the fact that my new variety is particularly characterized by its upright and vigorous growth of medium height, a free production of flower clusters which are relatively long-lasting on the plant, and the distinctively different color of the flowers, said color being Scarlet Red in the bud stage, changing to Rose Doree, lightly overcast with Scarlet Red, in the fully open flowers.

Asexual reproduction of my new variety by budding at Newark, New York, U. S. A., and at Pleasanton, California, U. S. A., shows that the foregoing characteristics and distinctions come true to form and are established and transmitted through succeeding propagations.

The accompanying drawing shows typical specimens of the flowers, stems and foliage of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Cinnabar."
- *Pollen parent.*—An unnamed seedling of "Cinnabar"×"Kathe Duvigneau."

Classification:
- *Botanic.*—Large-flowered polyantha.
- *Commercial.*—Floribunda.

FLOWER (Observations made from specimens grown outdoors at Newark, New York, U. S. A., in the early part of the month of August, and in the late morning.)

Blooming habit: Recurrent-continuous.

Bud:
- *Size.*—Large.
- *Form.*—Ovoid; is not affected by wet or hot weather.
- *Color.*—When sepals first divide—Pomegranate Purple, Plate 12. When petals begin to unfurl—Rose Red, Plate 12, lightly overcast with Pomegranate Purple, Plate 12. When half blown: Inside of petals—Scarlet Red, Plate 1; reverse of petals—Scarlet Red, Plate 1, lightly overcast with Rose Red, Plate 12.

- *Sepals.*—Slightly branched; curl back when petals begin to unfurl. Color: Inside—Kildare Green, Plate 31; outside—Light Hellebore Green, Plate 17.
- *Calyx.*—Color—Hellebore Green, Plate 17. Shape—funnel. Size—small. Aspect—smooth. Odor when rubbed—none.
- *Peduncle.* — Length — medium. Aspect — smooth. Strength—erect; slender. Color—Courge Green, Plate 17.
- *Opening.*—Opens up well; is not affected by adverse weather conditions.

Bloom:
- *Size.*—Medium. Average size when fully expanded—3½ inches to 4 inches.
- *Borne.*—In irregular clusters.
- *Stems.*—Medium length; normal strength.
- *Form (when first open).*—Cupped. Permanence—retains its form to the end, but outer petals curl back.
- *Petalage.*—Double (full but open center). Number of petals under normal conditions—from 25 to 30.
- *Color.*—Center of flower—Begonia Rose, Plate 1, lightly overcast with Scarlet Red, Plate 1. Outer petals—Begonia Rose, Plate 1. Base of petals (aiglet)—Naphthalene Yellow, Plate 16, Inside of petals—Rose Doree, Plate 1, lightly overcast with Scarlet Red, Plate 1. Reverse of petals—Rose Red, Plate 12, lightly overcast with Pomegranate Purple, Plate 12. General tonality from a distance—Begonia Rose, Plate 1.
- *Discoloration.*—General tonality at end of first day—Begonia Rose, Plate 1, lightly overcast with Scarlet Red, Plate 1. Second day—Rose Doree, Plate 1, lightly overcast with Scarlet Red, Plate 1. Third day—Rose Doree, Plate 1.

Petals:
- *Texture.*—Thick; is not affected by wet or hot weather.
- *Appearance.*—Inside—satiny; outside—shiny.
- *Form.*—Oval.
- *Arrangement.*—Irregular.
- *Petaloids in center.*—Few; small.
- *Persistence.*—Drop off cleanly.
- *Fragrance.*—Moderate. Nature—tea (average hybrid tea scent).
- *Lasting quality.*—On the plant—long; as cut flowers—long.

GENITAL ORGANS

Stamens, anthers: Medium size; many; regularly arranged around styles. Color—Apricot Buff, Plate 14.
Stamens, filaments (threads): Medium length. Color—Alizarine Pink, Plate 13.
Pollen: Color—Salmon Buff, Plate 14.
Styles: Bunched; uneven length; medium length; thin.
Stigmas: Color—Light Buff, Plate 15.
Ovaries: All enclosed in calyx.
Hips: None.
Seeds: None.

PLANT

Form: Bush.
Growth: Vigorous; upright; bushy;
Foliage: 5 to 7 leaflets.
- *Size.*—Medium.
- *Quantity.*—Abundant
- *Color.*—New foliage: Upper side—Chromium Green, Plate 32; under side—Oxblood Red, Plate 1. Old foliage: Upper side—Dark Cress Green, Plate 31; under side—Jade Green, Plate 31;
- *Shape.*—Oval pointed.
- *Texture.*—Upper side—glossy; under side—smooth.

*Ribs and veins.*—Ordinary.
*Edge.*—Serrated (saw-toothed).
*Serration.*—Both double and single; sharp.
*Leaf stem.*—Color—Light Grape Green, Plate 41. Under side—prickles.
*Stipules.*—Short; smooth.

Wood:

*New wood.*—Color—Carmine, Plate 1. Bark—smooth.
*Old wood.*—Color—Cress Green, Plate 31. Bark—smooth.

Thorns:

*Thorns.*—Quantity: On main stalks from base—ordinary; on laterals from stalk—ordinary. Form—broad base; medium length; hooked downward. Color (when young)—Spectrum Red, Plate 1. Position—irregular.

*Prickles.*—Quantity: On main stalks—none; on laterals—none.
*Short needles.*—Quantity: On main stalks—none; on laterals—none.

I claim:

A new and distinct variety of rose plant of the large-flowered polyantha class, substantially as herein shown and described, characterized particularly as to novelty by the vigorous and upright growth of the plant, the free production of its flower clusters of long-lasting quality on the plant, and the distinctive coloring of the flowers, said coloring being Scarlet Red in the bud stage, and being Rose Doree lightly overcast with Scarlet Red in the fully open flowers.

No references cited.